(12) United States Patent
Bentz

(10) Patent No.: US 10,000,323 B2
(45) Date of Patent: Jun. 19, 2018

(54) PACKAGES AND METHODS FOR MANUFACTURING PACKAGES

(71) Applicant: Bemis Company, Inc., Neenah, WI (US)

(72) Inventor: Aaron R. Bentz, Neenah, WI (US)

(73) Assignee: Bemis Company, Inc., Neenah, WI (US)

( * ) Notice: Subject to any disclaimer, the term of this patent is extended or adjusted under 35 U.S.C. 154(b) by 262 days.

(21) Appl. No.: 14/986,438

(22) Filed: Dec. 31, 2015

(65) Prior Publication Data

US 2017/0190492 A1    Jul. 6, 2017

(51) Int. Cl.
*B65D 33/00* (2006.01)
*B65D 75/58* (2006.01)
*B65D 75/52* (2006.01)
*A61B 50/30* (2016.01)

(52) U.S. Cl.
CPC .......... *B65D 75/5805* (2013.01); *A61B 50/30* (2016.02); *B65D 75/52* (2013.01); *B65D 75/5827* (2013.01); *B65D 75/5844* (2013.01); *A61B 2050/314* (2016.02)

(58) Field of Classification Search
CPC ............... B65D 75/5805; B65D 75/52; B65D 75/5827; B65D 75/5844; A61B 50/30; A61B 2050/314
USPC ............ 383/207–209, 111, 37, 38; 206/63.3
See application file for complete search history.

(56) References Cited

U.S. PATENT DOCUMENTS

| | | | | |
|---|---|---|---|---|
| 2,549,039 A | * | 4/1951 | Adams | A61B 17/06128 206/216 |
| 2,965,225 A | * | 12/1960 | Zoller | A61B 17/06119 206/63.3 |
| 3,017,990 A | * | 1/1962 | Singerman | A61F 15/001 206/440 |
| 3,279,595 A | * | 10/1966 | Blanford | B65D 59/04 206/440 |
| 3,368,740 A | | 2/1968 | Rohde | |
| 3,372,799 A | | 3/1968 | Abildgaard | |
| 3,405,863 A | | 10/1968 | Kugler | |
| 3,437,258 A | | 4/1969 | Kugler | |
| 3,809,228 A | * | 5/1974 | Fowler | B65D 75/28 206/306 |
| 3,870,150 A | * | 3/1975 | Hummel | B65D 75/30 15/227 |
| 3,917,160 A | * | 11/1975 | Olerud | B65D 75/52 383/111 |
| 3,959,948 A | * | 6/1976 | Fowler | B65B 5/02 53/473 |

(Continued)

*Primary Examiner* — Jes F Pascua
(74) *Attorney, Agent, or Firm* — Lynn M. Nett

(57) ABSTRACT

A package configured to contain and provide for sterile presentation of a product. The package includes a housing portion, a handling portion integrally formed with the housing portion, and a separation feature. The housing portion defines an interior product storage cavity and extends from a first end to a second end. The handling portion includes a cuff at the second end of the housing portion and a gripping portion extending from the cuff. The gripping portion is configured to extend inside the cuff and toward the storage cavity. The separation feature is disposed between the cuff and the housing portion, and the separation feature is configured to separate the housing portion and the handling portion.

15 Claims, 11 Drawing Sheets

(56) References Cited

U.S. PATENT DOCUMENTS

| | | | |
|---|---|---|---|
| 4,051,950 A * | 10/1977 | Jarund | B65B 9/02 |
| | | | 206/306 |
| 4,116,338 A | 9/1978 | Weichselbaum | |
| 4,294,360 A | 10/1981 | LeVeen | |
| 4,379,506 A | 4/1983 | Davidson | |
| 4,904,093 A | 2/1990 | Woods et al. | |
| 5,065,863 A * | 11/1991 | Moyet-Ortiz | A61B 42/40 |
| | | | 206/210 |
| 5,638,661 A | 6/1997 | Banks | |
| 5,704,670 A | 1/1998 | Surplus | |
| 5,816,403 A | 10/1998 | Wilkes et al. | |
| 6,203,080 B1 | 3/2001 | Surplus | |
| 6,578,348 B1 | 6/2003 | Banks | |
| 6,672,036 B2 | 1/2004 | Banks | |
| 7,718,433 B2 | 5/2010 | Stecklein et al. | |
| 7,731,701 B2 * | 6/2010 | Simon | B65D 75/20 |
| | | | 604/292 |
| 7,938,580 B2 | 5/2011 | Gaskell et al. | |
| 8,245,487 B2 | 8/2012 | Gammons | |
| 8,475,365 B2 | 7/2013 | Modin et al. | |
| 8,479,479 B2 * | 7/2013 | Howard | A41D 19/015 |
| | | | 53/461 |
| 8,479,918 B2 * | 7/2013 | Howard | A61B 42/50 |
| | | | 206/278 |
| 2005/0112758 A1 | 5/2005 | Archambault et al. | |
| 2006/0088450 A1 * | 4/2006 | Stecklein | A61L 2/07 |
| | | | 422/547 |
| 2014/0072247 A1 | 3/2014 | McDonough | |
| 2014/0270583 A1 * | 9/2014 | Anderson | B65D 31/04 |
| | | | 383/37 |
| 2015/0313682 A1 * | 11/2015 | Kowalewski | A61B 42/50 |
| | | | 604/292 |
| 2015/0313683 A1 * | 11/2015 | Kowalewski | A61B 42/50 |
| | | | 604/290 |

* cited by examiner

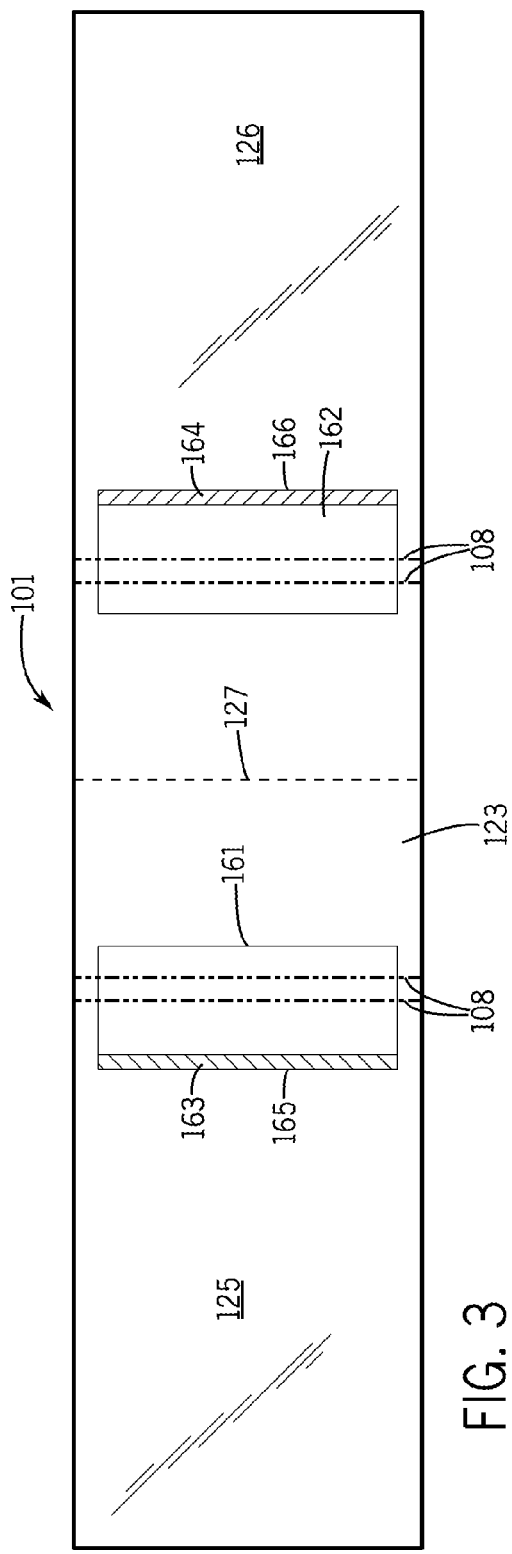
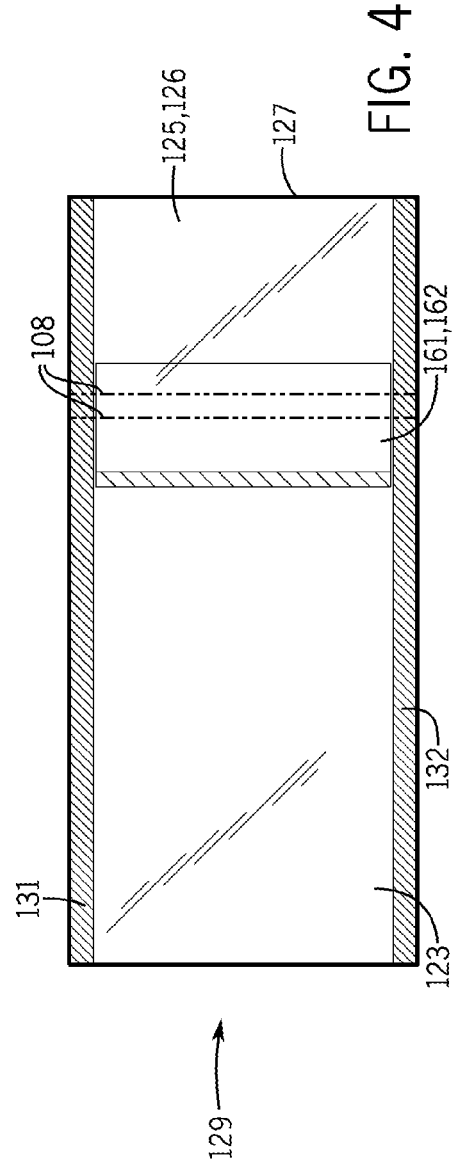

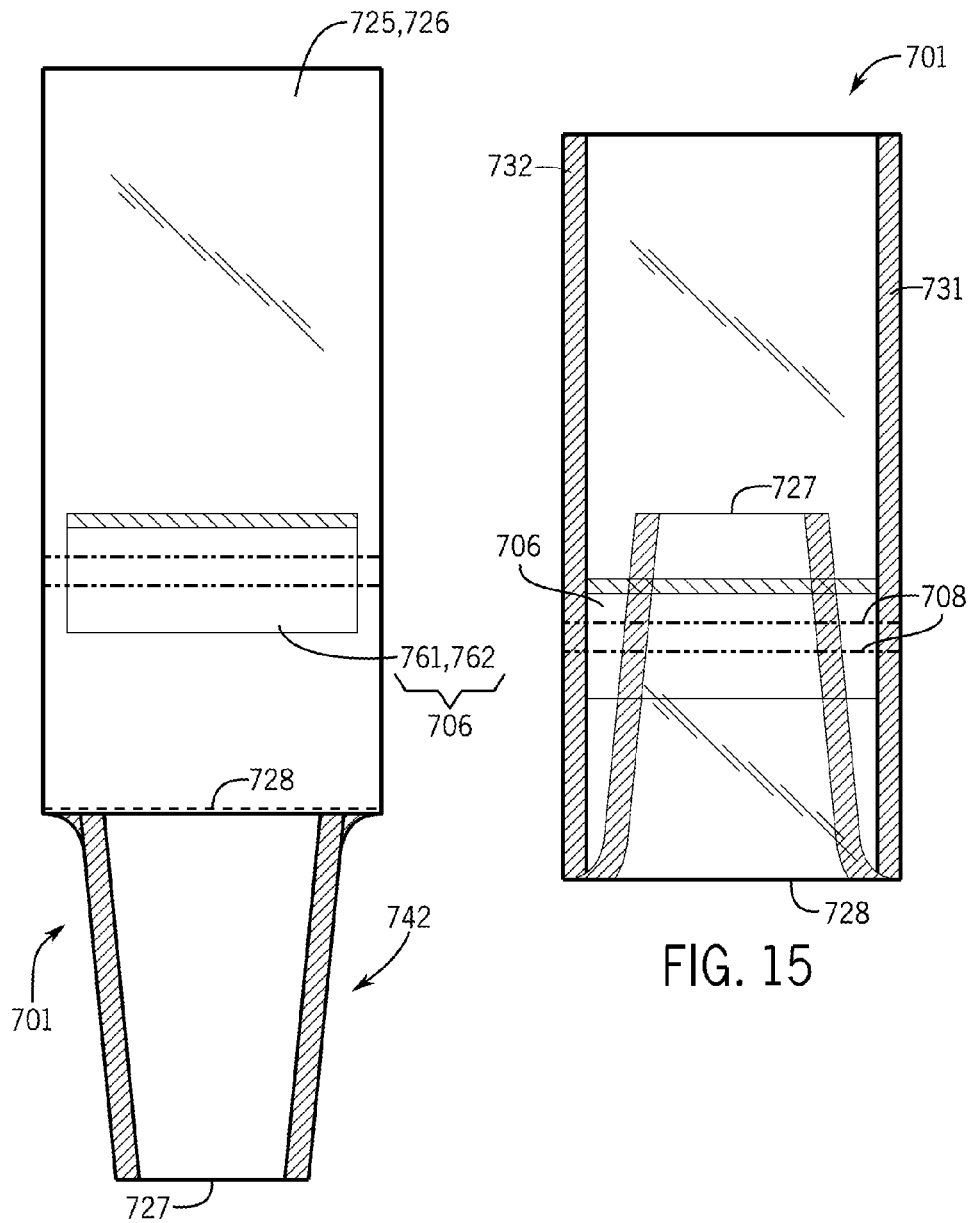

PACKAGES AND METHODS FOR MANUFACTURING PACKAGES

BACKGROUND

The present application relates generally to the field of packages for containing a product and methods for the manufacture of such packages. More specifically, this application relates to packages having a housing portion configured to contain a product and a handling portion that is separable from the housing portion and can be used to handle the product.

Packages are used to contain products in a generally enclosed space (e.g., environment), such as for transporting the products, protecting the products, or for other useful purposes. In certain applications, such as, for example medical related applications, it is necessary to maintain a sterile environment for the product so as to allow for a sterile presentation of the product (e.g., in the case of a medical device or product, to allow for the product to be easily removed from the package without compromising the sterile nature of the product). For these applications, exposure to non-sterile conditions/surfaces (e.g., the exterior of the package or something exterior to the package itself that can come into contact with the product, such as a hand of a medical professional) must be avoided to avoid contamination of the product and maintain the sterile presentation.

Thus, it is desirable to provide packages having an improved construction that allows for separation of the package into two portions. For example, the packages can be separated to provide an improved sterile presentation, such as by mitigating the risk of contamination of a contained product to maintain a sterile presentation. It is also desirable to provide a packages that simplifies the process of removing the product therefrom with a minimum number of hands/steps.

SUMMARY

One embodiment relates to a package configured to contain and provide for sterile presentation of a product. The package includes a housing portion, a handling portion integrally formed with the housing portion, and a separation feature. The housing portion defines an interior product storage cavity and extends from a first end to a second end. The handling portion includes a cuff at the second end of the housing portion and a gripping portion extending from the cuff (e.g., an end of the cuff that is opposite the second end of the housing portion). The gripping portion is configured to extend inside the cuff and toward the storage cavity. The separation feature is disposed between the cuff and the housing portion, and the separation feature is configured to separate the housing portion and the handling portion.

Another embodiment relates to a package configured to contain a product. The package includes a housing portion, a separation feature, and a handling portion. The housing portion includes a first panel coupled to a second panel at two opposing sides defining an interior product storage cavity, the housing portion also having a first end and a second end. The handling portion includes a cuff and a gripping portion. The cuff extends from the separation feature in a direction away from the housing portion, and the gripping portion extends from the cuff (e.g., an end of the cuff that is opposite the separation portion). The gripping portion includes a closed end that is configured to extend inside the cuff and through the second end of the housing portion into the storage cavity. The separation feature is disposed between the second end of the housing portion and the cuff, and the separation feature is configured to separate the housing portion and the handling portion.

Another embodiment relates to a package configured to contain a product. The package includes a panel and a separation feature. The panel includes a first edge coupled to a second edge, and the panel defines a housing portion and a handling portion extending from the housing portion. The housing portion defines an interior product storage cavity, and the handling portion includes a cuff and a gripping portion extending inside the cuff into the storage cavity. The separation feature is disposed between the cuff of the handling portion and the housing portion, and the separation feature is configured to separate the housing portion and the handling portion. The separation feature may be configured to separate the housing portion and the handling portion at the cuff.

Another embodiment relates to a method of manufacturing a package for providing a sterile presentation of a product housed in the package. The method includes providing a panel having a separation feature, coupling a protective portion to the panel at a first location, manipulating the panel such that a first side of the panel and a second side of the panel are in an adjacent and overlapping configuration, coupling the first and second sides of the panel together at a second location to form an open end and a closed end of the package, and forming a cuff surrounding a gripping portion by moving the closed end of the panel inside the protective portion toward the open end. The panel is configured to be separated at the separation feature to form a housing portion configured to house the product and a handling portion having the gripping portion configured to handle the product.

The first sheet of the protective portion may be coupled to the first side of the panel and a second sheet of the protective portion may be coupled to the second side of the panel, such that when the panel is folded about the fold line, at least a portion of the first sheet overlaps with at least a portion of the second sheet. The separation feature may include first and second lines of weakness that are laser scored into the panel.

Manipulating the panel may include folding one of the first and second sides of the panel about a fold line onto the other side of the panel, where the second location is a first edge of the first side to a first edge of the second side, and where a second edge of the first side is coupled to a second edge of the second side at a third location. Manipulating the panel may include rolling the panel such that two opposite edges are brought together, and where two opposite edges of the panel are coupled together at the second location. The closed end of the container may be formed by a heat seal.

Another embodiment relates to a method of manufacturing a package for providing a sterile presentation of a product housed in the package. The method includes providing a panel, providing a separation feature into the panel to facilitate separation of the panel, coupling a first sheet of a protective portion to a first portion of the panel, coupling a second sheet of the protective portion to a second portion of the panel, and folding the panel about a first fold line, such that the first and second portions of the panel at least partially overlap and the first and second sheets at least partially overlap. The method also includes coupling side edges of a gripping portion together, folding each of the first and second portions of the panel about a second fold line back onto the gripping portion such that the gripping portion is disposed between the first and second portions, and coupling the first and second sides of the panel together from the second fold line to an end opposite the gripping portion.

The side edges of the gripping portion may include a first notch in a first side and a second notch in a second, opposite side defining first and second notched edges, respectively. The first notched edges may be coupled together, such as using a heat seal, and the second notched edges may be coupled together, such as using a heat seal. The gripping portion may be configured to extend between the first and second sheets of the protective portion.

The first sheet of the protective portion may be coupled to the first portion of the panel using a first seal, such as a heat seal. The second sheet of the protective portion may be coupled to the second portion of the panel using a first seal, such as a heat seal.

The separation feature may include first and second lines of weakness that are scored into the panel. Each line of weakness may extend generally around the full periphery of the panel. Each line of weakness may be laser scored. Each line of weakness may be scored to a depth that does not fully penetrate a thickness of the panel. Each line of weakness may include a series of intermittent recesses into the panel.

BRIEF DESCRIPTION OF THE DRAWINGS

FIG. 3 is a plan view of the package shown in FIG. 1 prior to folding.

FIG. 4 is a plan view of the package shown in FIG. 1 after folding and sealing.

FIG. 14 is a plan view of the package shown in FIG. 13 after the first fold.

FIG. 15 is a plan view of the package shown in FIG. 13 after a second fold forming a gripping portion and after sealing.

DETAILED DESCRIPTION

Figure 1:
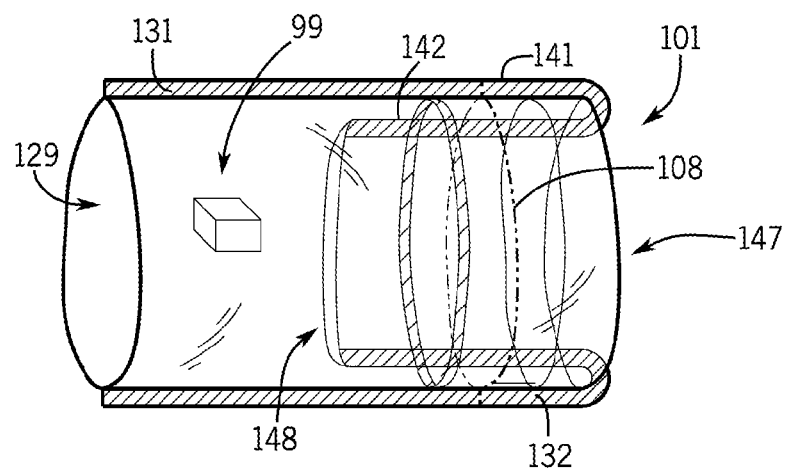
FIG. 1 is a perspective view of a package for containing a product according to an exemplary embodiment.

Referring generally to the FIGURES, disclosed in this application are packages (e.g., packaging, pouches, etc.) and methods of manufacturing (e.g., making, forming, assembling, etc.) such packages. The packages include a housing portion (e.g., sleeve, retainer, retaining portion, etc.) and a handling portion (e.g., gusset, grabbing portion, glove, etc.), which together form a structure (e.g., container) that can be configured to be airtight (e.g., form a hermetic seal). The housing portion is configured to contain (e.g., hold, retain, house, seal, enclose, etc.) a component (e.g., element, product, device, product, etc.). The handling portion may be inwardly facing and can be used to grip the component contained within the housing portion. The housing portion and handling portion may be configured to be separable, so as to allow for the removal of the component from the package. The packages may include one or more (e.g., two, four, etc.) features (e.g., lines of weakness, nicks, recesses, perforations, abrasions, areas or regions having differing material properties or orientations, etc., generally referred to herein as "weakening features") that are configured to facilitate separation between the housing portion and the handling portion so as to allow for removal of the component from within the package. For example, the weakening feature may include two lines of weakness configured to form a removable section (e.g., a tear strip) that can be separated from both the housing portion and the handling portion to thereby open the package and separate the housing portion from the handling portion. According to other exemplary embodiments, a weakening feature may be incorporated into the package that doesn't result in a removable portion of the package, but yet still allows for relatively simple separation between the housing portion and handling portion.

According to an exemplary embodiment, the packages disclosed in this application are configured to allow for sterile presentation of a component contained therein, such as, for example, by providing a hermetic seal around a medical device to be presented by a medical professional to a surgeon during an operation. Advantageously, the packages disclosed herein may allow for sterile presentation of the component (e.g., by maintaining the component in an airtight sterilized enclosure) without the need to slide the component onto a surface (which may not be sterile) or to delicately remove the component out of the package without touching the sides of the package. According to an exemplary embodiment, the handling portion allows for the component to be gripped with a first hand while the housing portion and handling portion are separated with a second hand. The housing portion can then be removed with the second hand while continuing to grip the component (or a tray or other structure in which the component is located) in the first hand. The packages may include a protective portion (e.g., hood, flap, collar, etc.) configured to prevent contamination of the component resulting from contact with a non-sterile surface of the package (e.g., the outside surface) upon removal of the housing portion from the component (or the component from the housing portion). The protective portion may be coupled to the housing portion, such as the end of the housing portion proximate to the handling portion.

The packages can be constructed in several ways. One such example includes sealing a sheet or film used to form the package on three sides, in which one of the sealed sides (e.g., ends, edges, profiles, etc.) is inverted back into a cavity of the package to create the handling portion. The package may be formed from a single piece of material (e.g., web, panel, film, etc.), which can be pre-scored or post-scored, or from multiple pieces of material. For example, the package may utilize a multilayer film suitable for weakening by a scoring device (e.g., a laser) or other suitable device (e.g., mechanical methods including a blade or slitting wheel). The multilayer film may include a polyester, a nylon, and/or other suitable materials. The housing portion and handling portion are configured to be separable, such as via one or more than one weakening feature. For example, a section near a base of the handling portion of the package can be scored to create a line of weakness to serve as the weakening feature. One or more sheets forming the protective portion can, optionally, be coupled to the interior of the container to help ensure a sterile presentation, such as to allow for removal of the housing portion while eliminating or greatly reducing the potential for the non-sterile exterior surface of the housing portion to come into contact with the packaged component and/or the sterile surface of the handling portion handling the sterile component. Another such example involves a stand up package, in which the handling portion is formed via one or more folds without having to invert a portion of the package. This package may utilize a web that has been pre-scored and/or a protective portion coupled to the housing portion. Other such examples are discussed below.

Figure 2:
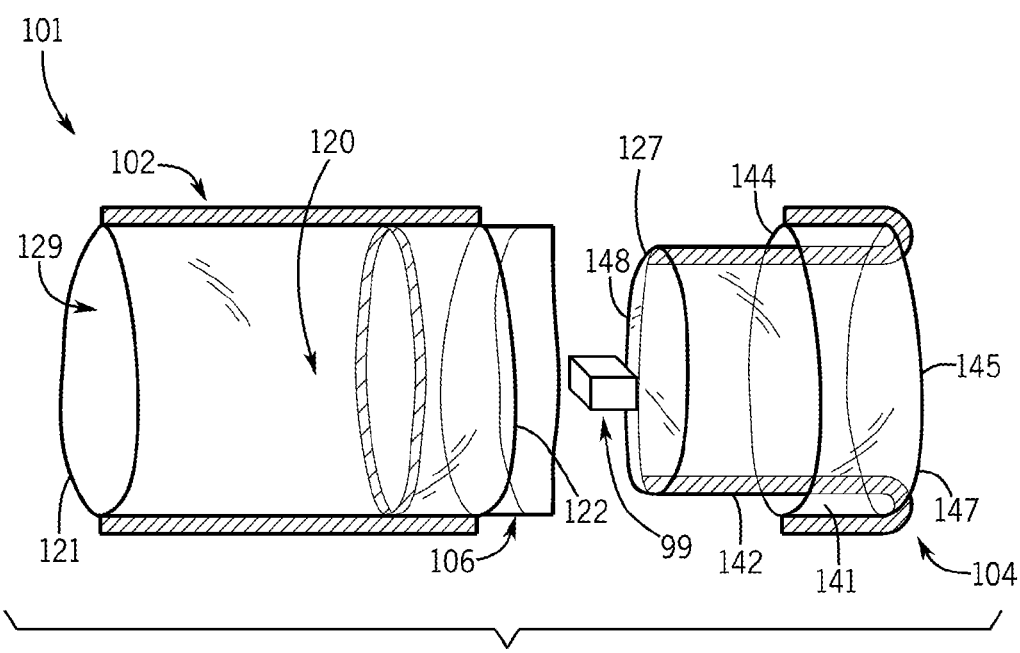
FIG. 2 is a perspective view of the package of FIG. 1 shown in a separated configuration that is intended to allow for removal of a product from the package.

Now referring specifically to the accompanying drawings, FIGS. 1 and 2 illustrate an exemplary embodiment of a package 101 that is configured to contain a product 99 (e.g., a component, device, element, object, etc.) therein. According to an exemplary embodiment, the package 101 is configured to contain a product, such as a medical device, in an interior cavity within the package 101 that is a sterile environment to help provide for a sterile presentation of the product. The product may include one element (e.g., a medical device, a medical instrument, etc.) or may include more than one element, such as, for example, a medical device inside of a carrier such as a tray or other structure. As non-limiting examples, the medical devices/instruments can be implantable devices (e.g., hip implants, stents, etc.), instruments (e.g., scalpels, scissors, syringes, sponges, etc.), or any other device/product that could benefit from being maintained in a sterile environment. Other sterile applications can involve pharmaceutical products, biotechnology products, food products, as well as any other product that would benefit from a sterile environment.

Other types of products can be contained in the packages disclosed herein according to other exemplary embodiments. For example, rather than maintaining a sterile presentation, the packages of this application could be configured to insulate (e.g., thermally, electrically, etc.) a user from the product contained in the package, such as by configuring the package to be insulating. Also for example, the packages disclosed herein may be configured to contain electronic components, mechanical components, specially coated surfaces, chemicals, microbiological materials, food products, halogen lamps or other products that may be detrimentally affected by interaction with human skin/oils, products including components toxic to humans, or any other types of products. The packages can provide anti-static or static-resistant enclosures for electronic components. As still another example, the packages can house mechanical components that are greasy (e.g., oily, lubricated, etc.) in an effort to prevent the spread of oil/lubricant to other elements or to maintain the necessary lubrication of the components prior to assembly or use.

The product can be placed (e.g., assembled, inserted, implanted, etc.) into the package 101 after assembly of the package 101, such as by a customer or other party, or may be assembled into the package during assembly of the package 101, as discussed below in more detail. The packages that, for example, are intended to help provide for a sterile presentation of the product can be sealed in a manner that is substantially impervious to air, bacteria, and other elements that would negatively impact the sterile environment. Typically, the sterilization process would be performed after the product is placed in the package.

As shown in FIGS. 1 and 2, the package 101 includes a housing portion 102, a handling portion 104, and a protective portion 106. Together, the housing portion 102 and the handling portion 104 are configured to form a package (e.g., pouch, bag, etc.), such as, for example, a structure of the package, that can contain the product 99 therein. The handling portion 104 is configured to be separable (e.g., detachable, removable, movable, etc.) from the housing portion 102, so as to allow access to the product (e.g., in the housing portion 102). Once separated, the handling portion 104 is configured to facilitate handling of the product. For the packages that help provide for a sterile presentation, the handling portion 104 is configured to act as a barrier between the hand(s) of a user (e.g., doctor, nurse, other suitable medical person or technician, etc.) and the sterile product (e.g., medical device, instrument, etc.) to maintain the sterile nature of the product prior to use (e.g., surgery, administration, etc.). It is noted that FIG. 1 shows the handling portion 104 and housing portion 102 prior to separation, and FIG. 2 shows the handling portion 104 separated from the housing portion 102.

The housing portion 102 is configured as a hollow member, shown generally tubular, that defines an interior cavity 120 for containing the product therein. As shown in FIGS. 1 and 2, the housing portion 102 of the package 101 is configured generally as a sleeve-shaped element that extends from a first end 121 to a second end 122. However, the housing portion 102 may be configured having other shapes (e.g., generally rectangular, generally cubic, etc.). Further, the housing portion 102 is made from a flexible material that allows the housing portion 102 to be reshaped (e.g., reconfigured, manipulated into other shapes, etc.).

The first end 121 of the housing portion 102 may be an open end (e.g., not sealed), so as to allow the product to be inserted into the cavity 120 through the open first end 121 after the package 101 is formed. The first end 121 may then be sealed using a heat seal or other suitable sealing process (the product may be inserted and the package sealed either by the package manufacturer or by a third party to which the package may be sent with the open first end 121).

The second end 122 of the housing portion 102 may be an open end to allow access to the product contained in the housing portion 102 after the handling portion 104 and the housing portion 102 are separated. As shown in FIG. 2, after the handling portion 104 and the housing portion 102 are separated, the product 99 can be accessed and removed through the open second end 122 of the housing portion 102.

The handling portion 104 is configured to form a structure of the package 101 (e.g., a container) with the housing portion 102. For example, the handling portion 104 may be integrally formed with the housing portion 102, such as from a single piece of material (e.g., a panel, film, etc.). According to other embodiments, the handling portion 104 may be formed separately from the housing portion 102 and coupled thereto, such as using a heat sealing or other suitable process. As shown in FIG. 1, the handling portion 104 is integrally formed with and extends from the second end of the housing portion 102. As discussed in more detail below, the handling portion 104, whether integrally formed with the housing portion 102 or formed separately and coupled with the housing portion 102, is configured to be separated from the housing portion 102 via a weakening feature (e.g., a line of weakness).

As shown in FIGS. 1 and 2, the handling portion 104 includes a cuff 141 (e.g., cover, outer sleeve, etc.) and a gripping portion 142 (e.g., hand enclosure, glove, bag, extrusion, protrusion, etc.). The cuff 141 is configured to surround the protective portion 106 prior to separation of the handling and housing portions 104, 102. This configuration is advantageous, for example, for the packages that help provide for a sterile presentation of a product, since the cuff 141 will maintain the sterile nature of the protective portion 106 prior to separation of the handling and housing portions 104, 102. Following separation of the handling and housing portions 104, 102, the sterile protective portion 106 reduces the risk of contamination of the sterile product during removal of the product from the housing portion 102, since the protective portion 106 is located at the end of the housing portion from which the product is being withdrawn. Thus, the risk of contacting the sterile product with a contaminated part of the package (e.g., the outside of the housing portion 102) is greatly reduced.

As shown in FIG. 2, the cuff 141 extends from a first end 144 to a second end 145. The first end 144 of the cuff 141 may be configured to extend from the housing portion 102, such as the second end 122 thereof. The first end 144 of the cuff 141 may be defined by a line of weakness, such that the first end 144 is separated from the housing portion 102 via the associated line of weakness. The second end 145 of the cuff 141 may define an end of the package 101.

The gripping portion 142 extends from the cuff 141. The gripping portion 142 may be integrally formed with the cuff 141, or formed separately from and coupled to the cuff 141. As shown in FIGS. 1 and 2, the gripping portion 142 is configured to extend inside (e.g., within) the cuff 141 and toward the protective portion 106 and/or the housing portion 102. The gripping portion 142 includes a first end 147, which extends from the second end 145 of the cuff 141, and a second end 148, which is provided within the housing portion 102 (prior to separation of the housing and handling portions, as shown in FIG. 1).

Figure 20:
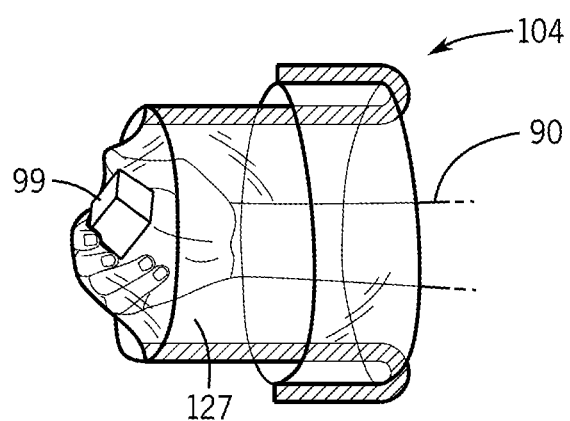
FIG. 20 is a perspective view of a person utilizing the handling portion of the package shown in FIG. 2 to grasp an object, such as to provide for a sterile presentation of the object.

The second end 148 of the gripping portion 142 is configured to face the product (housed in the housing portion) to allow a user to place a hand into the gripping portion 142 through the open first end 147 and use the closed second end 148 of the gripping portion 142 to grasp (e.g., hold, etc.) the product, such as to remove the product from the housing portion 102. FIG. 20 illustrates an arm 90 of a person extending into the open first end of the gripping portion 142 and grasping the object 99 using the closed second end of the gripping portion to help provide for a sterile presentation of the object 99. Thus, the closed second end is disposed between the person's hand and the object 99 to act as a barrier. This advantageously allows for a sterile product housed in the package to be grasped by the sterile side of the second end 148 of the gripping portion 142 to maintain the sterile presentation of the product.

The package 101 (e.g., the housing portion 102, the handling portion 104, etc.) may include one or more than one panel 123 (e.g., side, film, film subsection or portion, etc.) that defines the cavity 120, such as after being formed into the desired shape. Each panel 123 of the package is made from a flexible material that can be manipulated into any desired shape (e.g., through forming, folding, etc.) and is capable of forming an air-tight seal, such as when sealed. The material may be a single layer structure or a multilayer structure. For example, the material may include a nylon, polyethylene, a combination thereof, or any suitable polymer/plastic. Also for example, a multilayer film structure could include one or more layers configured to act as an oxygen barrier, a moisture barrier, a static barrier (e.g., anti-static), or provide other useful properties. According to one non-limiting example, each panel 123 is made from a PerfecForm® material from Bemis®. According to still other examples, generally oriented exterior web materials (e.g., oriented polyester, oriented nylon, oriented polypropylene, etc.) can be used and may be laminated to, for example, a polyolefinic (e.g., polyolefin) sealant. According to yet still other examples of materials that may be used include polyethylene, polypropylene, other polymers, as well as non-polymeric materials such as foils, papers, etc. The thickness of each panel 123 may be tailored to the design application, such as the weight of the product(s) to be housed in the package 101. According to one non-limiting example, the thickness of the material is approximately 2 to 6 mils. According to another non-limiting example, the material (e.g., of the container, film, panel, etc.) could be a basic structure having a 0.48 mil polyester film with a 1-2 mil polyethylene sealant.

A weakening (e.g., separation) feature may be employed to facilitate separation of the handling portion 104 and the housing portion 102. For example, one or more lines of weakness may be employed to facilitate separation between the handling portion and the housing portion. As shown in FIG. 1, the separation feature includes a single line of weakness 108, which is applied to the package to aid in the separation of the handling portion 104 and the housing portion 102. As shown in FIG. 3, the separation feature includes more than one line of weakness (e.g., two spaced apart lines of weakness 108) that are applied to each side (e.g., part, section, portion, etc.) of the panel 123.

Each line of weakness 108 may be scored into the panel 123 using a laser or other suitable device. Each line of weakness 108 may extend continuously (e.g., as a continuous or uninterrupted channel or region of decreased thickness, etc.) or intermittently (e.g., discontinuous regions of decreased thickness, such as a series of adjacent indentations or openings in the material), such as to provide a series of steps (e.g., notches, etc.) in the panel, along its length. If the scoring is intermittent, such as from pulsing the laser, the length of each score and the distance between successive scorings may be tailored to the design application, such as to allow separation at a desired force. A depth of the scoring into the panel 123 (e.g., penetration) may also be tailored to the design application, such as to influence the separation force. For packages configured to help provide for a sterile presentation of a product, the scoring will not fully penetrate the thickness of the material at any location that would defeat the sterility by allowing contaminates (e.g., in air) to pass through into the cavity configured to house the product(s). For an intermittent scoring, the depth of each step/notch may be uniform or may be different. The use of a laser to score the panel 123 may advantageously provide for greater control and/or more precision with respect to the scoring process. For example, the laser may be configured (e.g., by adjusting its frequency) to remove only certain materials or portions of certain materials. By way of example, if the material of the panel 123 includes more than one layer of different types of materials (e.g., a layer of nylon, a layer of polyethylene), then the laser can be configured to remove only select portions of the one layer while leaving the other layer to maintain the sterile presentation.

Each line of weakness 108 may be formed using other techniques or weakening features. For example, a segment of tear tape could be used to facilitate separation between the handling and housing portions of the container. The tape could be disposed between a portion of the handing portion and a portion of the housing portion, such that upon application of a threshold force the tape either tears or breaks to allow separation of the two portions. Also for example, a peelable delaminate (e.g., sticker, film, etc.) may be employed to facilitate separation between the housing and handling portions, such as upon application of a threshold force.

Figure 18:
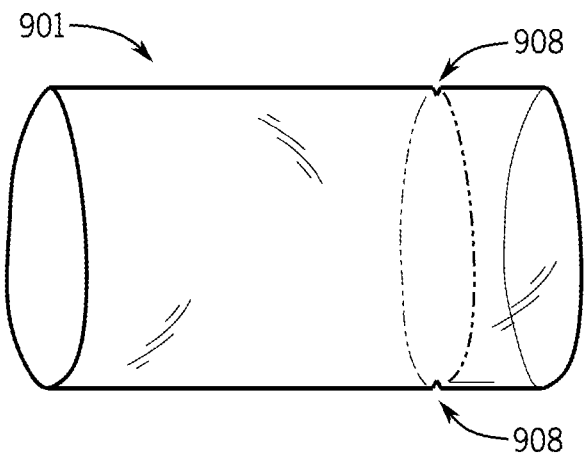
FIG. 18 is a perspective view of a package according to yet another exemplary embodiment.
Figure 19:
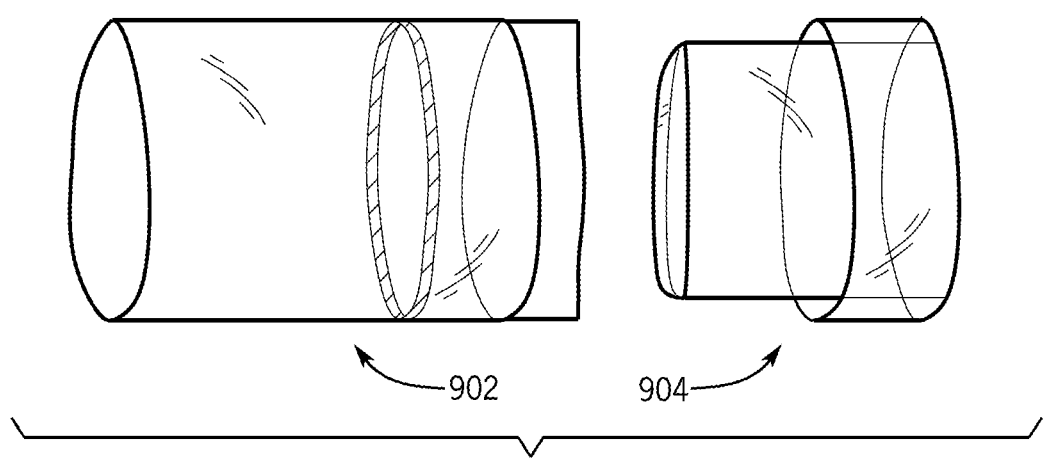
FIG. 19 is a perspective view of the package shown in FIG. 18 in a separated configuration to allow for removal of a product form the package.

According to other examples, the weakening feature may include one or more nicks (e.g., indentations, notches, dimples, etc.) placed into the package to facilitate tearing along the one or more nicks. The number of nicks and the location of each nick in the package can be tailored to the design application. As shown in FIG. 18, the package 901 includes two tear initiators 908 (e.g., nicks, notches, tabs, cutouts, thumb notches, etc.) in the unitary package to facilitate separating the container into a housing portion 902 and a handling portion 904, as shown in FIG. 19. According to an exemplary embodiment, the two tear initiators 908 are provided in the container at substantially the same location (e.g., length relative to an end or other feature of the package, such as the protective portion) to control the location of tearing of the container, such that a first tear propagating from the first nick 908 (e.g., lower nick) will meet a second tear propagating from the second nick 908 (e.g., upper nick). Thus, the location of the nicks may be configured to provide a single tear in the package that is generally planar. According to another exemplary embodiment, the two tear initiators 908 are provided in the package at different locations (e.g., at different lengths from an end or other feature of the package), such that two offset tears are formed in the package, with one tear propagating from each nick. The size (e.g., area, depth, diameter, etc.) of each nick 908 can be tailored to the design application, such as based on the thickness and/or material properties of the package. For the packages configured to help provide sterile presentations, the nicks do not fully penetrate the package (e.g., the depth of each nick is less than the thickness of the material forming the container) to maintain the sterile environment in the package. It may be advantageous to utilize the tear initiators in conjunction with an oriented film that is aligned properly to propagate the tear in a desired manner or any other linear tear material (e.g., an ionomer-EVA blend film).

Each panel may be formed using a material that further aids controlling the location of tearing of the package from each nick 908. For example, the material of the container may have relatively weak tear properties to further control the location of tearing of the package. Also for example, the material may be a monolayer film configured to tear in a linear fashion. The linear direction of tearing can be tailored to the specific design application to control tearing of the package.

The protective portion 106 is configured to help maintain the sterile presentation when removing the product from the package 101. The package 101 may also be configured without the protective portion 106 at all, such as for non-sterile applications. As shown in FIGS. 1 and 2, the protective portion 106 is coupled to an interior surface (e.g., inside) of the housing portion 102 proximate the open second end 122 thereof. At least a portion of the protective portion 106 extends beyond the second end 122 of the housing portion 102 and between the cuff 141 and the gripping portion 142. This portion of the protective portion 106 helps maintain the sterile presentation, such as by reducing the risk of contamination of the sterile product (housed in the package 101) during removal of the product from the housing portion 102.

The protective portion 106 is shown made from a flexible material that can be manipulated into any desired shape (e.g., through forming, folding, etc.) and is capable of being sealed to the package. For example, the material may include a nylon, polyethylene, a combination thereof, or any suitable polymer/plastic. According to one non-limiting example, the protective portion 106 is made from a Perfec-Form® material from Bemis®. Generally, the protective portion 106 can be configured as a sterile surface that overhangs (e.g., extends beyond an end of) the housing portion 102 toward the gripping portion.

FIGS. 3-7 illustrate various stages of assembly of exemplary embodiments of methods of manufacturing (e.g., assembling) packages, such as the package 101 or any other package disclosed in this application. One exemplary embodiment of a method of manufacturing the package 101 includes a six step process. Although the six steps may be described below using sequential terms (e.g., first, second, third, etc.), the order of the steps can be rearranged (e.g., switched) according to one of skill in the art of packages.

One step of the method (e.g., the first step) includes providing a panel 123 of material to form the cavity of the package 101. According to one embodiment, the panel 123 is formed by unrolling a section of a roll of material and cutting (e.g., blanking, trimming, etc.) a piece (e.g., panel, strip, segment, section, etc.) of the material to a desired size (e.g., length). According to another embodiment, the panel 123 is formed by cutting a flat sheet of material to the desired size. Accordingly, the cavity of the package 101, as shown in FIGS. 3 and 4, is formed using a single, continuous (e.g., interconnected, etc.) panel 123.

Another step of the method (e.g., the second step) includes providing (e.g., forming, scoring, etc.) one or more than one line of weakness into the panel 123 to facilitate separation between the housing portion 102 and the handling portion 104. As shown in FIG. 3, two spaced apart lines of weakness 108 are applied to each of the first and second sides 125, 126 of the panel 123, and each line of weakness 108 extends between the top and bottom edges of each side. The two lines of weakness 108 are shown to be parallel, but the two (or more) lines of weakness 108 can be configured in a non-parallel manner. Providing two lines of weakness is more advantageous, such as for helping to provide for a sterile presentation of a product, because having two lines allows a user to remove the strip formed between the two lines to more easily separate the two portions while maintaining the sterile presentation. According to an exemplary embodiment, each set of two lines of weakness 108 are located a common distance from a fold line 127, such that upon folding the first and second sheets 125, 126 onto one another about the fold line 127, the two sets of lines of weakness 108 will overlay one another. The two lines of weakness 108 of each set may be separated by a common distance. As shown in FIG. 3, each line of weakness 108 extends to the edges of the respective side 125, 126 of the panel 123. However, each line of weakness 108 may be configured to extend a different length for other examples.

Another step of the method (e.g., the third step) includes providing (e.g., coupling, attaching, securing, sealing, etc.) the protective portion to the panel 123. As shown in FIG. 3, the protective portion includes a first sheet 161, which is coupled to an inner surface of a first side 125 of the panel 123, and a second sheet 162, which is coupled to an inner surface of a second side 126 of the panel 123. Each sheet 161, 162 has a length and a width, which may be tailored to the specific design application. According to an exemplary embodiment, the length of each sheet 161, 162 is less than the distance between the seal of the top edges (e.g., the first seal 131) and the seal of the bottom edges (e.g., the second seal 132). In this way, each sheet 161, 162 may advantageously not extend into the sealed portions of the panels, such as to impede separation of the housing portion 102 and the handling portion 104. According to another exemplary embodiment, the length of each sheet 161, 162 extends into one or both of the seals of the top edges (e.g., the first seal 131, the second seal 132). Each sheet that extends into one (or more) seal can include a weakening feature, as disclosed elsewhere in this application, such as to facilitate separation of the housing portion 102 and the handling portion 104.

Each sheet 161, 162 may be coupled to the panel 123 using any suitable method (e.g., island placement, die cut lid-style, label-style application, etc.). According to an exemplary embodiment, each sheet 161, 162 is sealed to the panel 123 using a heat seal, such as through the application of heat and/or pressure. For example, each seal may be formed through a weld heat seal by application of heat and pressure to the panel 123 and/or the associated sheet 161, 162, with their respective adjacent surfaces in contact with each other for a time that is sufficient to cause bonding, such as before and/or during cooling of the sealed area. As shown, a portion of an end 165 of the first sheet 161 is heat sealed to a corresponding adjacent (e.g., abutting) portion of the first side 125, which is illustrated by a cross-hatched area 163 (see FIG. 3); and a portion of an end 166 of the second sheet 162 is heat sealed to a corresponding adjacent portion of the second side 126, which is illustrated by a cross-hatched area 164. An adhesive (e.g., a permanent adhesive) can also be used to form each seal, either alone or in combination with another sealing technique (e.g., heat seal). For example, an adhesive (e.g., a pressure sensitive adhesive) can be sandwiched between the two adjacent surfaces (e.g., the inner surface of panel 123 and the outer surface of the associated sheet 161, 162) to secure the surfaces together, such as upon the application of pressure. Each seal can be configured to be a permanent seal (e.g., resistant to peeling) or can be tailored to a specific peel force, depending on the design application. As another example, each sheet of the protective portion 106 may be sealed to the panel 123 using an ultrasonic seal, such as through the application of ultrasonic acoustic vibrations. It is noted that the order of the second and third steps could be switched, such that the scoring is performed after the protective portion is coupled to the panel 123.

Another step of the method (e.g., the fourth step) includes folding one side of the panel 123 onto the other side of the panel. FIG. 3 shows the fold line 127 about which the one side (e.g., the first side 125, the second side 126) of the panel 123 is folded onto the other side. As shown in FIG. 4, the panel 123 is folded about the fold line 127 such that the two sides 125, 126 of the panel 123 are configured in a stacked manner (i.e., with one side on top of the other side). The panel 123 can be configured to be symmetric (e.g., symmetrically opposite), as shown FIG. 3, such that after folding, the first and second sheets 161, 162 are provided adjacent to one another in an overlying and stacked configuration (see FIG. 4). The lines of weakness 108 can be configured such that the lines of weakness 108 in the second side 126 overly the lines of weakness 108 in the first side 125 (or vice versa).

Another step of the method (e.g., the fifth step) includes sealing the panel 123 to form the cavity. As shown in FIG. 4, the top edges of the two sides 125, 126 of the panel 123 are sealed together and the bottom edges of the two sides 125, 126 are sealed together. Thus, a first seal 131 is formed between the top edge of the first side 125 and the top edge of the second side 126; and a second seal 132 is formed between the bottom edge of the first side 125 and the bottom edge of the second side 126. Each of the first and second seals 131, 132 may be formed using any method/process disclosed in this application (e.g., heat seal, adhesive, etc.) or any other suitable method/process. By sealing the top and bottom edges, a cavity having three closed sides and one open side is formed. The three closed sides include the two seals 131, 132 and the side defined by the fold line 127, with the open side 129 (e.g., open end) opposite the fold line side. The open side 129 allows for the product to be placed into the cavity.

Another step of the method (e.g., the sixth step) includes forming the gripping portion 142. According to an exemplary embodiment, the gripping portion 142 is formed by manipulating (e.g., moving, pushing, etc.) the side defined by the fold line 127 back into the package 101 toward the open side 129. The fold line side of the handling portion may be moved into the cavity through the opening defined by the first sheet 161 and the second sheet 162 to form the gripping portion 142 (shown in FIG. 1) having the first end 147 open and the second end 148 facing the open side 129. The gripping portion 142 may extend from a cuff of the handling portion back inside (e.g., within) the cuff. The open first end 147 allows a user to place a hand into the gripping portion 142 therethrough and use the closed second end 148 of the gripping portion 142 to grasp (e.g., hold, clasp, etc.) a product in the cavity 120, such as to remove the product from the housing portion 102. The package 101 may be manipulated further to provide additional features/shape. For example, the fold line side can be pushed back into the gripping portion 142, such that the fold line side faces away from the open side 129 and toward the open first end 147.

Figure 21:
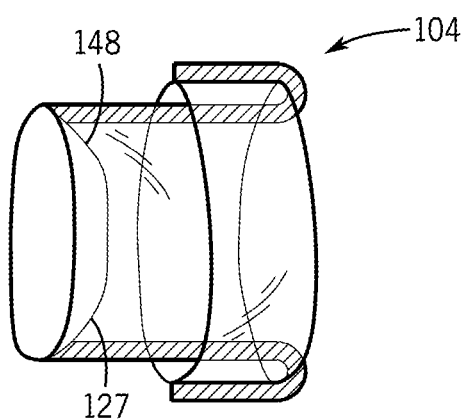
FIG. 21 is a perspective view of the handling portion of the package shown in FIG. 2, further manipulated to form a W-fold at the handling end.

As shown in FIG. 21, the gripping portion of the handling portion 104 may be further manipulated, such as, for example, to form a "W" shape at the closed second end 148. The fold line 127 can be manipulated (e.g., moved, pushed, etc.) back into the handling portion toward the open first end (through which a person can insert their arm) to form the inverted "V" shaped portion of the "W" shape. A person can place their hand into the gripping portion, such that the apex of the inverted "V" shaped portion points toward (or rests in) the palm of their hand with their fingers extending between one wall defining the inverted "V" shape and the outer wall of the handling portion forming the "W" shape, and with their thumb extending between the other wall defining the inverted "V" shape and the other outer wall of the handling portion forming the "W" shape. This arrangement may advantageously make it easier for the person to grasp the object, since the gripping portion acts as a mitten. It is noted that the gripping portion of the handling portion 104 may be manipulated in other ways. For example, the gripping portion may be manipulated in a manner to form fingers for receiving the fingers of the person's hand extending into the handling portion.

Figure 5:
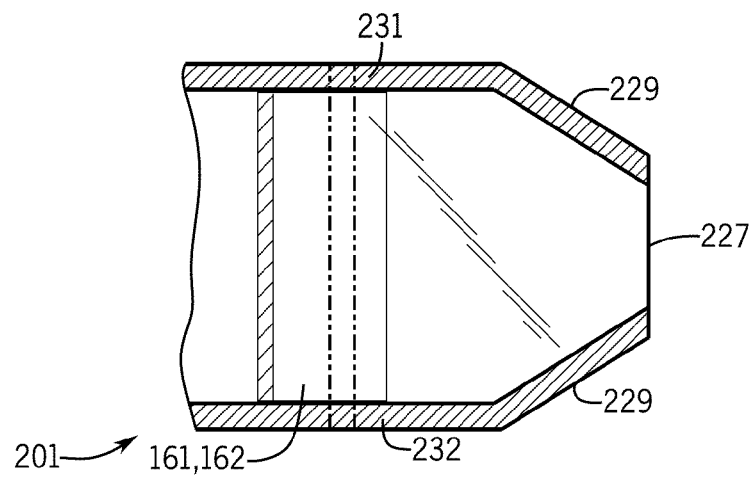
FIG. 5 is a plan view of a portion of a package having a pouch according to another exemplary embodiment.

FIG. 5 illustrates a portion of another exemplary embodiment of a package 201, which can be manufactured using the six step process described above for the package 101. However, where the package 101 has an end after folding along the fold line 127 that is generally orthogonal, as shown in FIG. 4, the package 201 may be configured such that the end defined by the fold line 227 is not orthogonal. As shown in FIG. 5, the end may include oblique corner sections 229, which may be formed by notching each of the top and bottom edges of the panel 123 with a generally "V" shaped notch having an apex (i.e., the point of the V) on the fold line 227. This notching step can be done as a separate step or combined with the trimming step (e.g., the first step). Once the sides of the package 201 have been folded onto one another forming the fold line 227, a first seal 231 is created along the top edge and the top corner section 229 and a second seal 232 is created along the bottom edge and the bottom corner section 229. The oblique corner sections 229 may make the step of forming the bag easier, since the wedge shape of the end formed by the corner sections 229 and the fold line 227 makes inserting the end back into the opening formed by the first and second sheets 161, 162 easier.

Another exemplary embodiment of a method of manufacturing a package (e.g., the packages 301, 401 shown in FIGS. 6 and 7) involves a different six step process. The packages 301, 401 do not include a fold line (e.g., the fold line 127, 227), which has been replaced by another seal, as discussed below. Although the steps may be described below using sequential terms (e.g., first, second, third, etc.), the order of the steps can be rearranged (e.g., switched) in any order and the order described is not limiting in nature.

Figure 6:
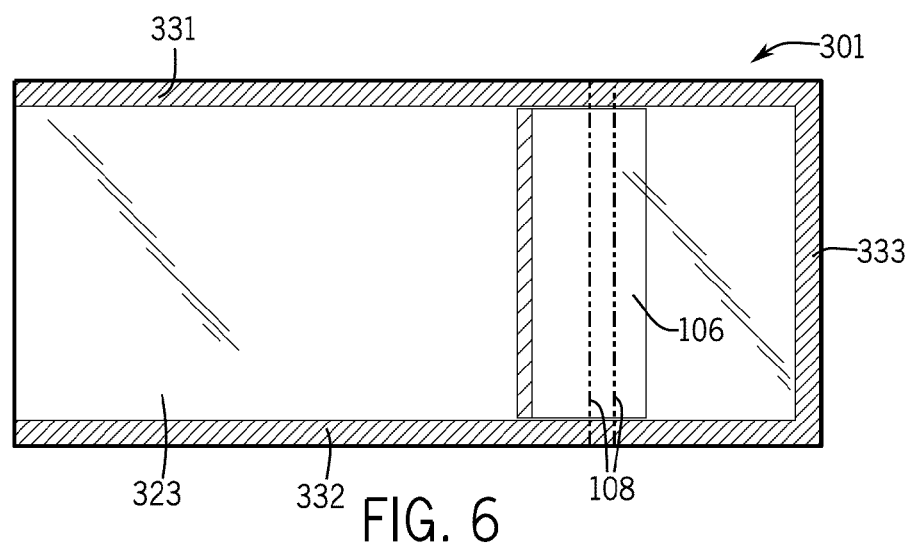
FIG. 6 is a plan view of a package according to another exemplary embodiment.
Figure 7:
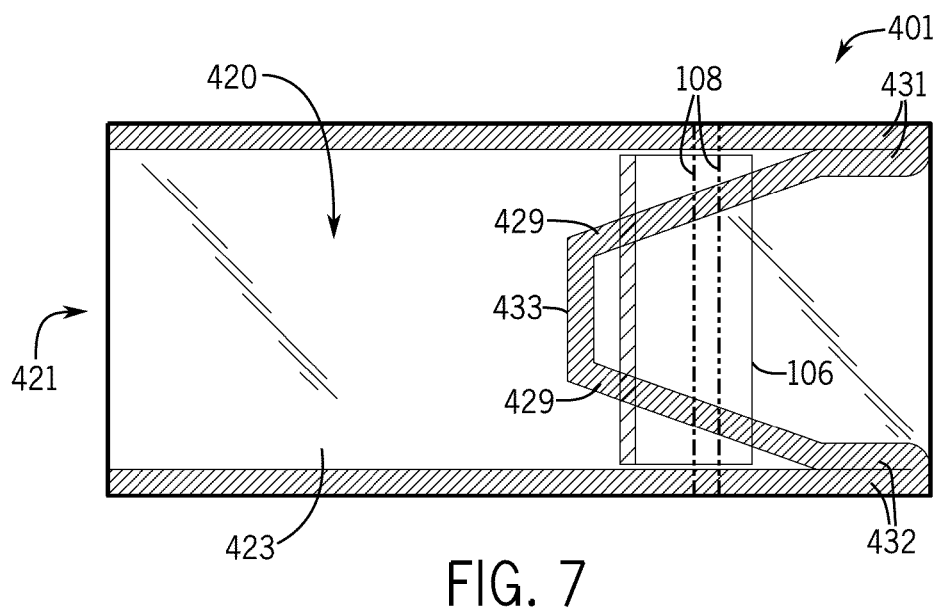
FIG. 7 is a plan view of a package according to another exemplary embodiment.

One step of the method (e.g., the first step) includes providing two separate panels of material, which will be used to form the container of the package 301, 401. Each panel 323, 423 may have a generally rectangular shape with orthogonal ends (e.g., as shown in FIG. 6), may have an end with oblique portions (e.g., as shown on in FIG. 7), or may have any other suitable shape. The two panels 323 for the package 301 are configured substantially the same; and the two panels 423 for the package 401 are configured substantially the same.

Additional steps of the method (e.g., the second step, the third step) includes one of providing a separation feature (e.g., one or more lines of weakness 108) into each panel 323, 423 to facilitate separation between the housing portion and the handling portion, and coupling the protective portion 106 to each panel 323, 423.

Another step of the method (e.g., the fourth step) includes bringing together the two panels 323 for the package 301 (or the two panels 423 for the package 401), such that one panel overlies the other panel, with the two sheets of the protective portion 106 sandwiched between the two panels. Thus, the protective portion 106 is located between the two panels.

Another step of the method (e.g., the fifth step) includes coupling (e.g., sealing) the two panels 323, 423 together to form the cavity. For the package 301 shown in FIG. 6, the top edges of the panels 323 are coupled at a first seal 331, the bottom edges of the panels 323 are coupled at a second seal 332, and the right edges (e.g., ends) of the panels 323 are coupled at a third seal 333. For the package 401 shown in FIG. 7, the top edges of the panels 423 are sealed at a first seal 431, the bottom edges of the panels 423 are sealed at a second seal 432, and the ends of the panels 423 are sealed at a third seal 433. The oblique sections 429 of the package 401 are also sealed. The seals 331, 332, 333, 431, 432, 433, etc. may be formed using any technique disclosed in this application. For example, the seals 331, 332, 333, 431, 432, 433, may be heat seals, adhesive seals, etc.

Another step of the method (e.g., the sixth step) includes forming/defining/positioning the gripping portion of the handling portion. The gripping portion can be formed using the same processes as disclosed elsewhere in this application or using a different process.

Figure 8:
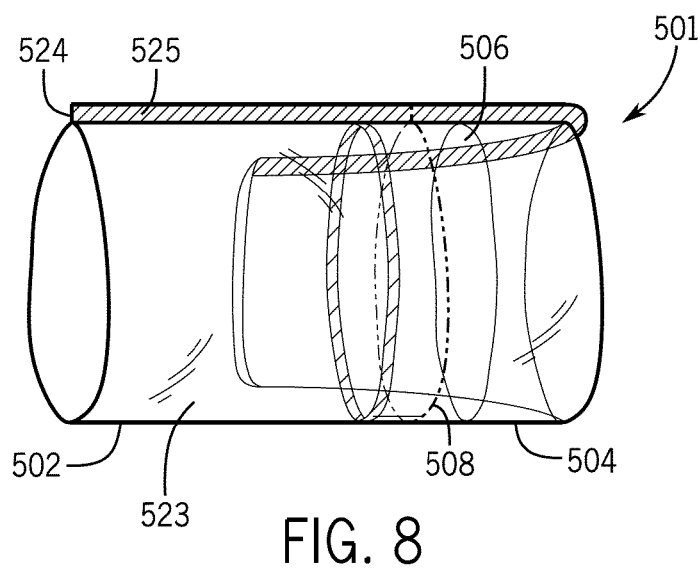
FIG. 8 is a perspective view of a package according to another exemplary embodiment.
Figure 9:
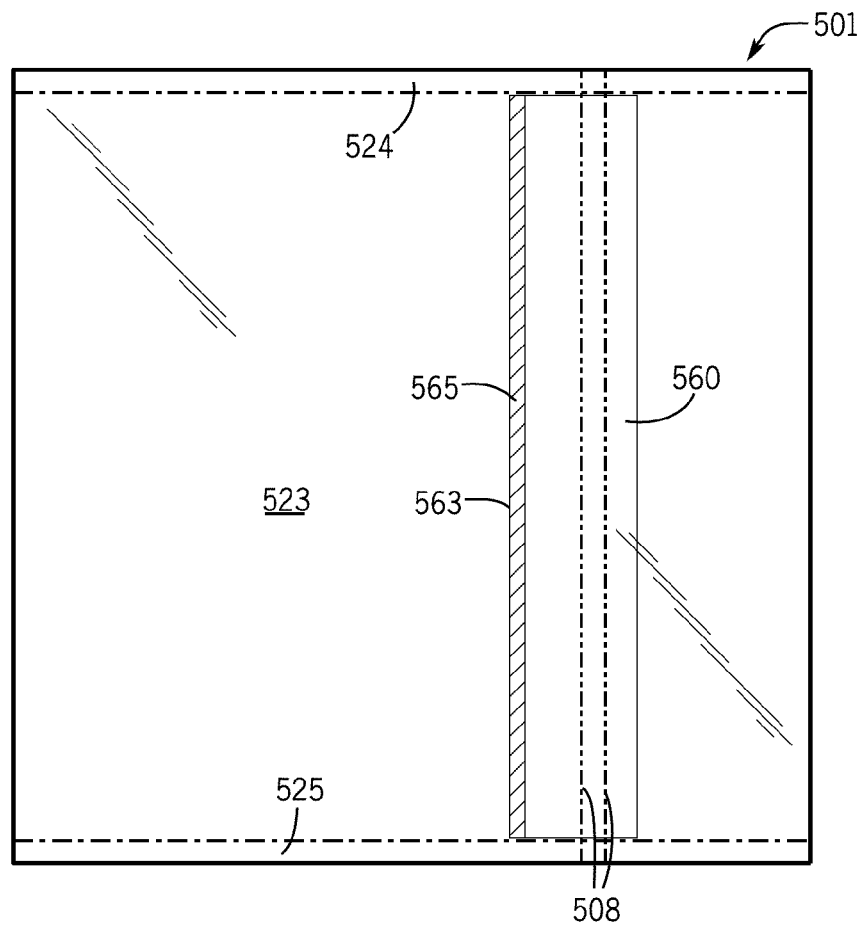
FIG. 9 is a plan view of the package shown in FIG. 8 prior to forming.

FIGS. 8-11 illustrate another exemplary embodiment of a package 501 that includes a panel 523 that is configured to form both the handling portion 504 and the housing portion 502. As shown in FIG. 9, the panel 523 includes a first side (e.g., upper side, top side, right side, etc.) seam portion 524 and a second side (e.g., lower side, bottom side, left side, etc.) seam portion 525, which are configured to be coupled together, as shown in FIG. 8. Extending across the panel 523, such as from an upper edge of the upper seam portion 524 to a lower edge of the lower seam portion 525, are two lines of weakness 508, which may be configured according to any line of weakness (e.g., the line of weakness 108) disclosed herein.

The package 501 may include a protective portion 506. As shown in FIG. 9, a protective portion 506 in the form of a single sheet 560 is configured to extend between a lower edge of the upper seam portion 524 and an upper edge of the lower seam portion 525. The sheet 560 is configured to overly at least a portion of each line of weakness 508. At least a portion of the sheet 560 is coupled to the panel 523. As shown in FIG. 9, the left end 563 of the sheet 560 is coupled to the sheet 560, such as, for example, via a heat seal 565 (which is shown using a cross-hatched area).

Figure 10:
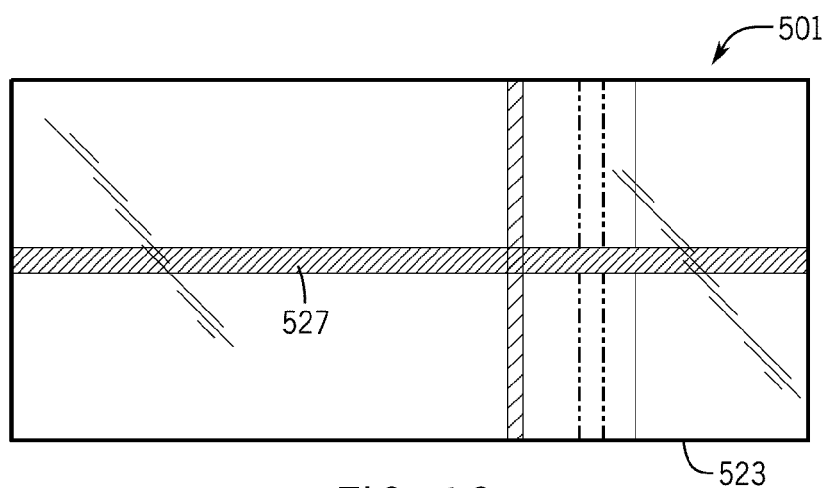
FIG. 10 is a plan view of the package shown in FIG. 8 after forming and sealing.

As shown in FIG. 10, the panel 523 is formed (e.g., folded, rolled, etc.) such that the upper seam portion 524 and the lower seam portion 525 are brought together and coupled together, such as, for example, via a heat seal 527 (which is shown using a cross-hatched area). Each heat seal can be configured as a lap seal, a fin seal, or any other suitable seal. Together, the coupled portions 524, 525 may form a seam that extends the length of the package 501, as shown in FIG. 8.

Figure 11:
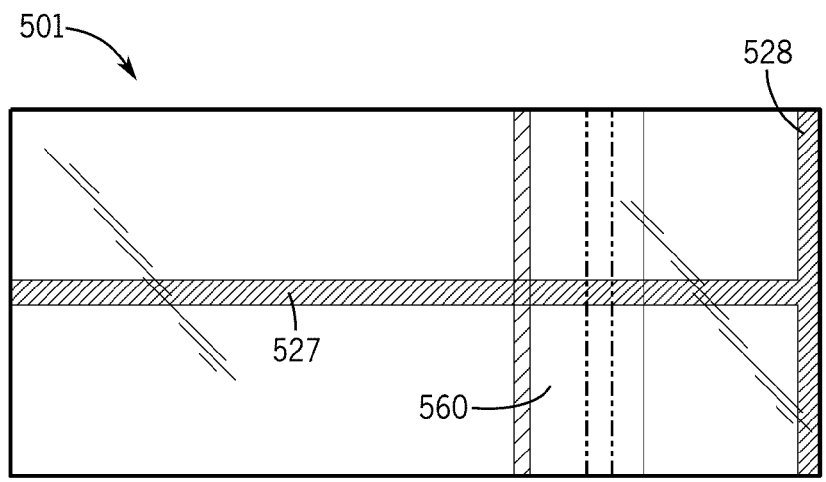
FIG. 11 is a plan view of the package shown in FIG. 8 after forming and sealing a seam and an end.

As shown in FIG. 11, one of the two open ends of the package 501 may be closed via a seal, such as a heat seal 528. The closed end of the package 501 (e.g., the heat seal 528) may be pushed back into the cavity of the package 501, such as inside the sheet 560 to form the handling portion 504 having a gripping portion (e.g., gusset) and/or a cuff.

Figure 12:
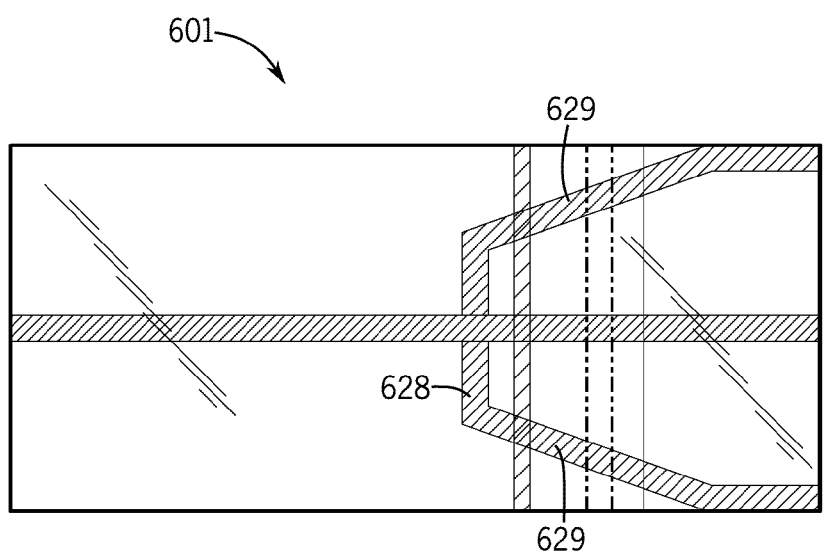
FIG. 12 is a plan view of the package shown in FIG. 8 after forming a gripping portion.

FIG. 12 illustrates another exemplary embodiment of a package 601. The package 601 may be configured similar to the package 501, except the closed end of the package 601 has two oblique corner sections 629 extending from the heat sealed end 628, rather than having a generally orthogonal end, as shown in FIG. 11. As shown in FIG. 12, each oblique corner section 629 may be configured to extend within the protective portion.

Figure 13:
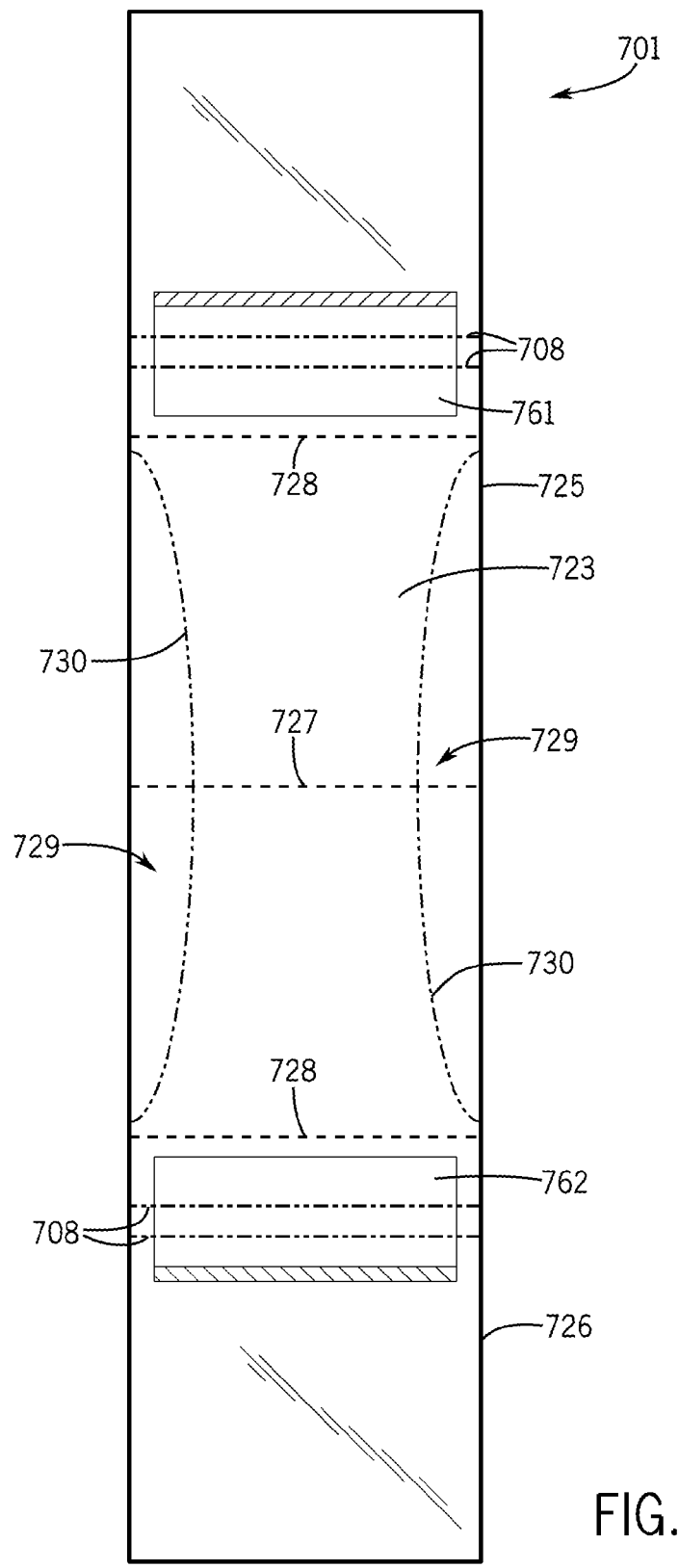
FIG. 13 is a plan view of a package according to another exemplary embodiment and shown prior to a first fold.

FIGS. 13-15 illustrate another exemplary embodiment of a package 701. The package 701 may be configured as a pouch, which can be folded along a first fold line 727 and a pair of second fold lines 728. As shown in FIG. 13, a panel 723 of material is provided and a protective portion is coupled thereto. The protective portion may include a first sheet 761 coupled to a top section 725 of the panel 723 and a second sheet 762 coupled to a bottom section 726 of the panel 723. The package 701 may include a weakening feature. The weakening feature may include, for example, one or more lines of weakness 708 that are placed into the panel 723, such as by laser scoring. As shown, each sheet 761, 762 overlays at least a portion of two lines of weakness 708 of the weakening feature.

The panel 723 also includes two notches 729, with one notch 729 in each side of the panel 723. As shown in FIG. 13, each notch 729 extends lengthwise between the two second fold lines 728, with each notch 729 being defined by a trim line 730 (showed as phantom style lines). Each notch 729 may be configured to extend any distance widthwise, so long as some section of the panel 723 remains. The notches 729, the lines of weakness 708, and the sheets 761, 762 may be performed in any order to manufacture the package 701.

The panel 723 having the sheets 761, 762 is then folded along the first fold line 727, such that the top and bottom sections 725, 726 overly one another, with the sheets 761, 762 also overlying one another (see FIG. 14) to define (e.g., form) the handling portion 742. Then the outer side profiles of the handling portion 742 are sealed using any suitable method (e.g., heat seal). Thus, the handling portion 742 is sealed on three sides, with the first fold 727 acting as one seal and the two sealed side profiles acting as the other two seals.

The panel 723 having the sheets 761, 762 is then folded along each of the second fold lines 728 to form the shape shown in FIG. 15. Thus, the top and bottom sections 725, 726 having the sheets 761, 762 are folded back onto the handling portion 742, such that a gripping portion of the handling portion 742 is disposed (e.g., sandwiched) between the top and bottom sections 725, 726. Again, the sheets 761, 762 overly one another, as do the lines of weakness 708.

The first side 731 of the top and bottom sections 725, 726 of the panel 723 are sealed together, and the second side 732 of the top and bottom sections 725, 726 of the panel 723 are sealed together using any suitable method (e.g., heat seal). For this method, the gripping portion of the handling portion 742 does not have to be manipulated into position by pushing it through the protective portion 706, because the handling portion 742 is already in this position due to the folding processes.

Figure 16:
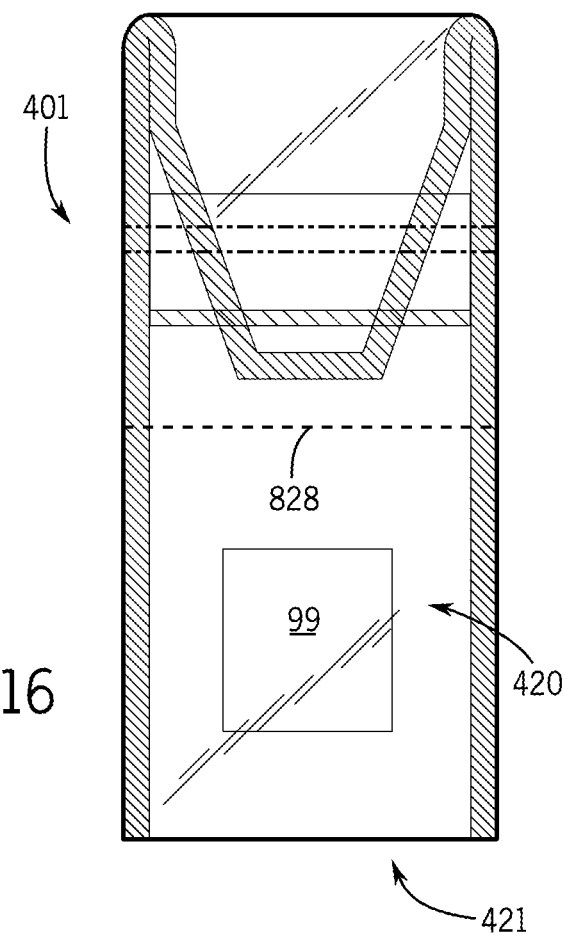
FIG. 16 is a plan view of a package, such as the package shown in FIG. 7, with a fold line illustrated.
Figure 17:
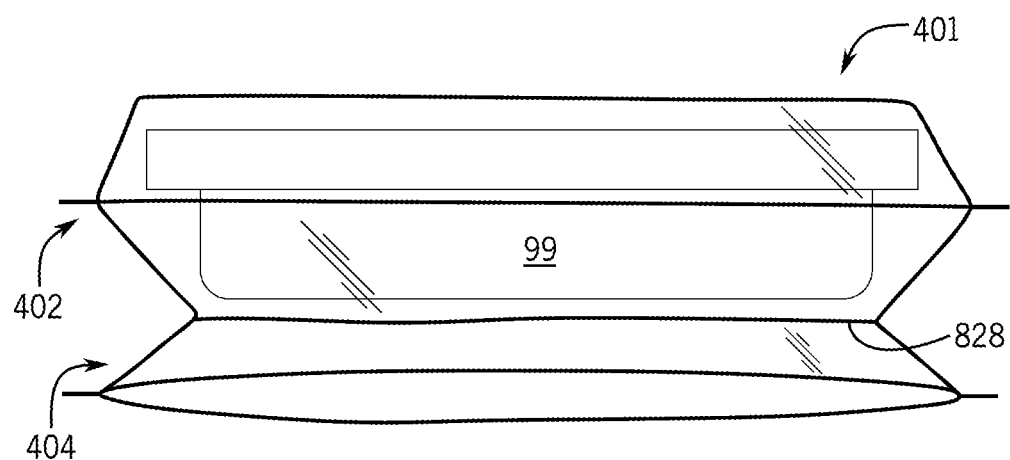
FIG. 17 is a front view of the package shown in FIG. 16 folded along the fold line.

FIGS. 16 and 17 illustrate that a package 401 can be folded to decrease the size (e.g., length) of the package. The package 401 can be configured as described above (for FIG. 7). A product (e.g., the product 99) can be inserted into the cavity 420 through the open end 421 of the package 401. After the product 99 is inside the package 401, the open end 421 package 401 can be sealed using any suitable technique (e.g., heat seal). If the product 99 is intended to be for sterile presentation, the package 401 can be sterilized using any suitable technique. After sealing the end 421, such that the end 421 is a closed end, the package 401 can be folded along the fold line 828 to reduce the overall length of the package 401, which may advantageously make it easier to transport (e.g., carry) the package 401. As shown in FIG. 17, after folding, the housing portion 402 can be above (e.g., on top of) the handling portion 404. According to another example, the housing portion 402 can be below (e.g., underneath) the handling portion 404 after folding.

If desired, the package 401 can be sterilized to provide a sterile presentation of the product 99. As non-limiting examples, the package 401 can be gamma irradiated, exposed to ethylene oxide, or any other suitable sterilization process. Such sterilization process will generally be performed after a product is placed into the package.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The terms "coupled," "connected," and the like, as used herein, mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

The construction and arrangement of the elements of the packages, as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements, the position of elements may be reversed or otherwise varied, and the nature or number of discrete elements or positions may be altered or varied.

Additionally, the word "exemplary" is used to mean serving as an example, instance, or illustration. Any embodiment or design described herein as "exemplary" is not necessarily to be construed as preferred or advantageous over other embodiments or designs (and such term is not intended to connote that such embodiments are necessarily extraordinary or superlative examples). Rather, use of the word "exemplary" is intended to present concepts in a concrete manner. Accordingly, all such modifications are intended to be included within the scope of the present disclosure. Other substitutions, modifications, changes, and omissions may be made in the design, operating conditions, and arrangement of the preferred and other exemplary embodiments without departing from the scope of the appended claims.

Other substitutions, modifications, changes and omissions may also be made in the design, operating conditions and arrangement of the various exemplary embodiments without departing from the scope of the present invention. For example, any element (e.g., panel, sheet, line of weakness, seal, etc.) of the packages disclosed in one embodiment may be incorporated or utilized with any other embodiment disclosed herein. Also, for example, the order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes and omissions may be made in the design, operating configuration, and arrangement of the preferred and other exemplary embodiments without departing from the scope of the appended claims.

What is claimed is:

1. A package configured to contain and provide for sterile presentation of a product, the package comprising:
   (a) a housing portion defining an interior product storage cavity, the housing portion extending from a first end to a second end;
   (b) a handling portion integrally formed with the housing portion, the handling portion comprising:
   (i) a cuff at the second end of the housing portion; and
   (ii) a gripping portion extending from the cuff, the gripping portion being configured to extend inside the cuff and toward the storage cavity;
   (c) a separation feature disposed between the cuff and the housing portion, the separation feature configured to separate the housing portion and the handling portion; and
   (d) a protective portion coupled to an interior surface of the housing portion, such that at least a portion of the protective portion extends beyond the second end of the housing portion; wherein the cuff is configured to surround the protective portion prior to separation of the handling and housing portions.

2. The package of claim 1, wherein each of the first end and the second end of the housing portion is an open end, and the open first end is configured to receive the product therethrough.

3. The package of claim 2, wherein two edges of the first end of the housing portion are configured to be coupled together after the product is placed in the storage cavity, and wherein the package is sterilized.

4. The package of claim 1, wherein the gripping portion is configured to extend inside of the protective portion.

5. The package of claim 1, wherein the protective portion comprises:
   a first sheet coupled to an inner surface of a first side of the housing portion; and
   a second sheet coupled to an inner surface of a second side of the housing portion.

6. The package of claim 5, wherein a first edge of each of the first and second sheets is coupled to the associated side of the housing portion, and a second, opposite edge of each of the first and second sheets extends beyond the second end of the housing portion.

7. The package of claim 1, wherein the separation feature comprises a first line of weakness that is configured to extend generally around the full periphery of the package.

8. The package of claim 7, wherein the separation feature further comprises a second line of weakness offset from the first line of weakness, such that the two lines of weakness define a removable strip; and wherein the second line of weakness is configured to extend generally around the full periphery of the package.

9. The package of claim 8, wherein at least one line of weakness overlies the protective portion.

10. The package of claim 9, wherein the housing portion includes a side extending between the first and second ends, the side of the housing portion being sealed, and wherein the protective portion does not extend into the sealed side of the housing portion.

11. The package of claim 1, wherein the gripping portion further comprises a closed end that includes at least one of a heat seal and a fold.

12. The package of claim 1, wherein the gripping portion further comprises a closed end that includes at least two folds.

13. A package configured to contain a product, the package comprising:
   a panel having a first edge coupled to a second edge, the panel defining a housing portion and a handling portion extending from the housing portion, the housing portion defining an interior product storage cavity, the handling portion comprising a cuff and a gripping portion extending inside the cuff into the storage cavity; and
   a separation feature disposed between the cuff of the handling portion and the housing portion, the separation feature being configured to separate the housing portion and the handling portion, and
   wherein the housing portion and handling portion are formed from a single panel.

14. The package of claim 13, wherein a first end of the panel is open and a second end of the panel is closed, the closed second end of the panel defining the gripping portion.

15. The package of claim 14, wherein a heat seal couples the first edge of the panel to the second edge of the panel, wherein the package further comprises a protective portion coupled to an interior surface of the panel, such that at least a portion of the protective portion extends beyond an end of the housing portion, the cuff is configured to surround at least a portion of the protective portion prior to separation of the handling portion and the housing portion, and at least a portion of the separation feature crosses at least a portion of the protective portion.

* * * * *